United States Patent [19]
Sriram et al.

[11] Patent Number: 5,959,241
[45] Date of Patent: Sep. 28, 1999

[54] SCANNING FORCE MICROSCOPE THERMAL MICROPROBE

[75] Inventors: Tirunelveli Subramanian Sriram, Maynard, Mass.; Robert B. Marcus, Murray Hill, N.J.; Yongxia Zhang, Tempe, Ariz.

[73] Assignee: Digital Equipment Corporation, Houston, Tex.

[21] Appl. No.: 09/070,640

[22] Filed: Apr. 30, 1998

[51] Int. Cl.[6] .................................................... H01L 35/28
[52] U.S. Cl. ......................... 136/228; 136/233; 136/201; 136/236.1
[58] Field of Search ..................... 136/200, 201, 136/224, 228, 229, 233, 236.1; 438/758

*Primary Examiner*—Kathryn Gorgos
*Assistant Examiner*—Thomas H Parsons
*Attorney, Agent, or Firm*—Hamilton, Brook, Smith & Reynolds, PC

[57] ABSTRACT

A small bimetallic thermocouple probe device for use in scanning atomic force microscopy is mass produced by etching and oxidatively sharpening silicon points on a standard silicon wafer. The sharpened points are oxidized and the first thermocouple metal layer is deposited and patterned. The intermetal dielectric layer is deposited and removed in the area of the tip of the probe by a simple double spin photoresist process having a drying cycle between the two spins. The exposed tips have the dielectric etched, and the second thermocouple metal is deposited and patterned. The finished thermocouples are produced by etching the silicon from the back side of the wafer to free up the cantilevered structure which the probe are constructed upon. With such a procedure, large numbers of tiny, low thermal mass scanning atomic force microscope thermocouple probes may be inexpensively manufactured.

5 Claims, 8 Drawing Sheets

SCANNING FORCE MICROSCOPE THERMAL MICROPROBE

BACKGROUND OF THE INVENTION

This invention relates generally to methods for exposing selected small regions of layers of materials on needle shaped objects, and more particularly to fabrication of thermocouples and probes for scanning force microscopes.

As is known in the art, the manufacture of probe tips for what are known as scanning force microscopes requires precise control of dimensions and shapes. The probe tips, known as microprobes, are generally elongated metallic structures having highly sharpened tips containing the microprobe detector. Examples of various microprobe detectors known in the art include tunneling current, magnetic field detectors and thermal detectors. In particular, typical thermal microprobes use sharp needles comprised of two different metals, known as a bimetallic thermocouple, where the area of the contact region between the two different metals is one of the important control features, along with the atomic composition of the two metals and the amount of contamination in the contact region. It is difficult to control the contact area of the bimetallic thermocouple because of the difficult geometry of the sharp needle tip.

A known method for making bimetallic thermocouples for use in scanning microprobes (known as thermal microprobes) is to coat a sharpened needle with a first dielectric layer, a first metal layer and a second dielectric layer. The tip of the needle is held close to a metal plate and a large enough voltage is applied to the first metal layer to cause the second dielectric layer to rupture, causing a contact region to form. The second metal layer of the thermocouple is deposited to form the required bimetallic layer.

However, such a method is not effective for providing reproducible thermal microprobes because the area of the contact region between the two different metals is neither carefully controlled, adjustable nor reproducible. Thus the manufacturing yields of good thermocouple probes is reduced, consequently the cost of thermal microprobes is increased, and the sensitivity of the thermal microprobes varies from probe to probe, requiring difficult calibration procedures.

Thus, the prior art has two distinct problems with bimetallic layers for thermal microprobes. The first problem is forming small reproducible low resistance contact regions on sharp needle like structures, which may result in poor manufacturing yields due to variable contact resistance between the two metal layers, and incompletely opened contacts. The second problem is that the contacts are not of a preselectable or uniform size, resulting in various sized contact regions and variable thermocouple performance and sensitivity. The smaller the contact area between the two metal layers the less the thermal mass of the thermocouple and the faster the temperature response can be. This feature is particularly important in the scanning force microscope field since it impacts the maximum possible scanning speed. Such small reproducible thermal microprobes may be used in scanning force microscopes to perform real time measurements on operating integrated circuits, in effect providing the ability to watch a microscopic integrated circuit function in a normal fashion.

SUMMARY OF THE INVENTION

In accordance with the invention, a method for exposing a controlled area of a tip region of an elongated structure is disclosed, comprising the steps of first coating the elongated structure with a first metal layer, coating with a dielectric layer and applying a layer of a liquid organic compound to the dielectric layer to expose a controlled area of the tip region, and removing the dielectric layer in the controlled area of the tip. The controlled area of the tip region is exposed by a spinning process of applying a liquid organic compound of a controlled low viscosity to the elongated structure, spinning for a predetermined time and rotational speed, drying the liquid organic compound for a predetermined time, forming a semisolid skin, and spinning the organic compound for a second predetermined time and rotational speed such that the tip region protrudes through the liquid organic compounds skin.

In another embodiment, the tip region is exposed by means of a controlled etch back of the liquid organic compound, or by a controlled blanket partial exposure of a low viscosity photoresist layer and subsequent development cycle to partially remove the photoresist by controlled thinning of the photoresist layer.

In yet another embodiment of the invention the semiconductor material of the sharp tip itself is heavily doped and effectively becomes the first metal layer of the bimetallic thermocouple.

With such an arrangement a reproducible sharp thermal microprobe tip is produced, variation in metal to metal contact size is reduced with a concomitant increase in both thermocouple variability and uniformity. Such an arrangement also provides improved ability to make small contact areas with acceptable uniformity resulting in improved thermal sensitivity.

BRIEF DESCRIPTION OF THE DRAWINGS

The foregoing features of this invention, as well as the invention itself, may be more fully understood from the detailed description read together with the accompanying drawings, in which.

DESCRIPTION OF THE PREFERRED EMBODIMENT

Figure 1:
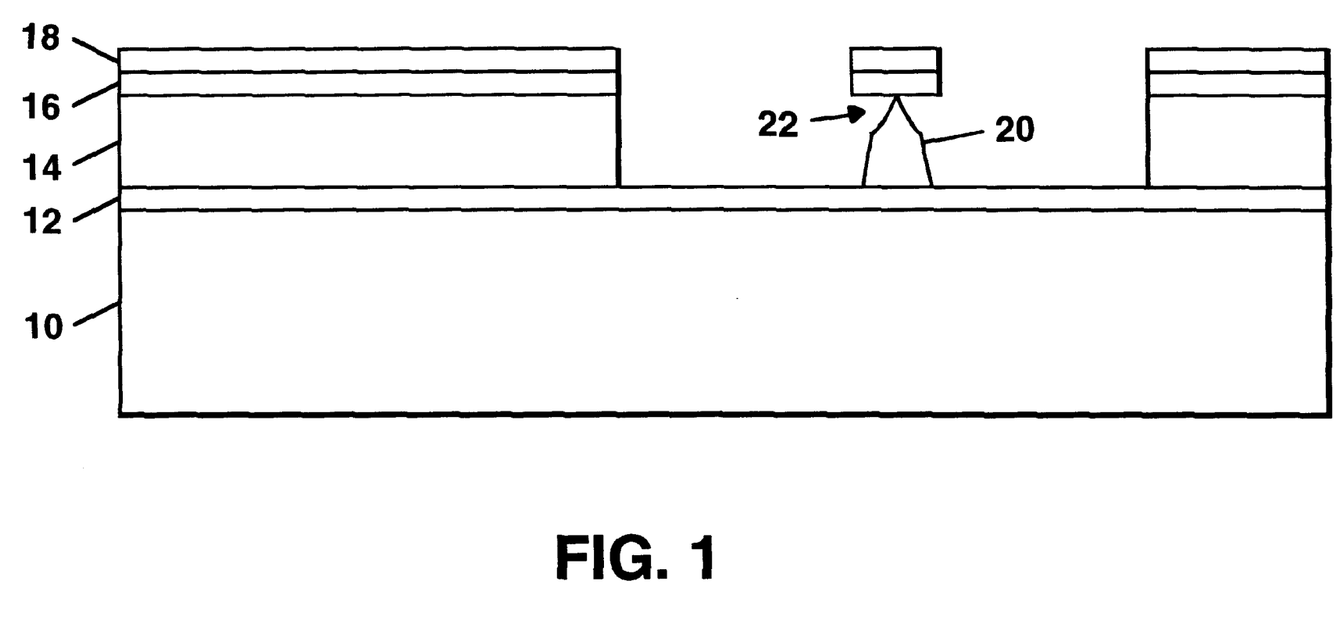
FIG. 1 is a cross sectional view of the fabrication process in accordance with the invention.

Referring now to FIG. 1, a semiconductor substrate 10, typically silicon, has a specific doping level and type. In the preferred embodiment the substrate is silicon with a light doping of an N type. The substrate 10 includes a heavily doped surface layer 12, preferably of a P+ type. In particular, this P+ semiconductor layer is intended to represent an etch stop layer for the fabrication of the microprobe cantilever structure described later in this specification. Another semiconductor layer 14 is formed, preferably by epitaxial deposition, upon the doped surface layer 12. Layer 14 is preferably silicon and has a preferably heavy doping level of type N++ to be electrically conductive and metal like. A dielectric layer 16, preferably silicon dioxide, and a patternable layer 18, preferably photoresist, are formed upon layer 14. The photoresist 18 is defined and the dielectric layer 16 is etched, by any of the well known methods. The semiconductor layer 14 is then etched, preferably initially with an isotropic etch to produce the double recurved region 22, and secondly with an anisotropic etch to produce the remainder of an elongated needle like structure 20.

Figure 2:
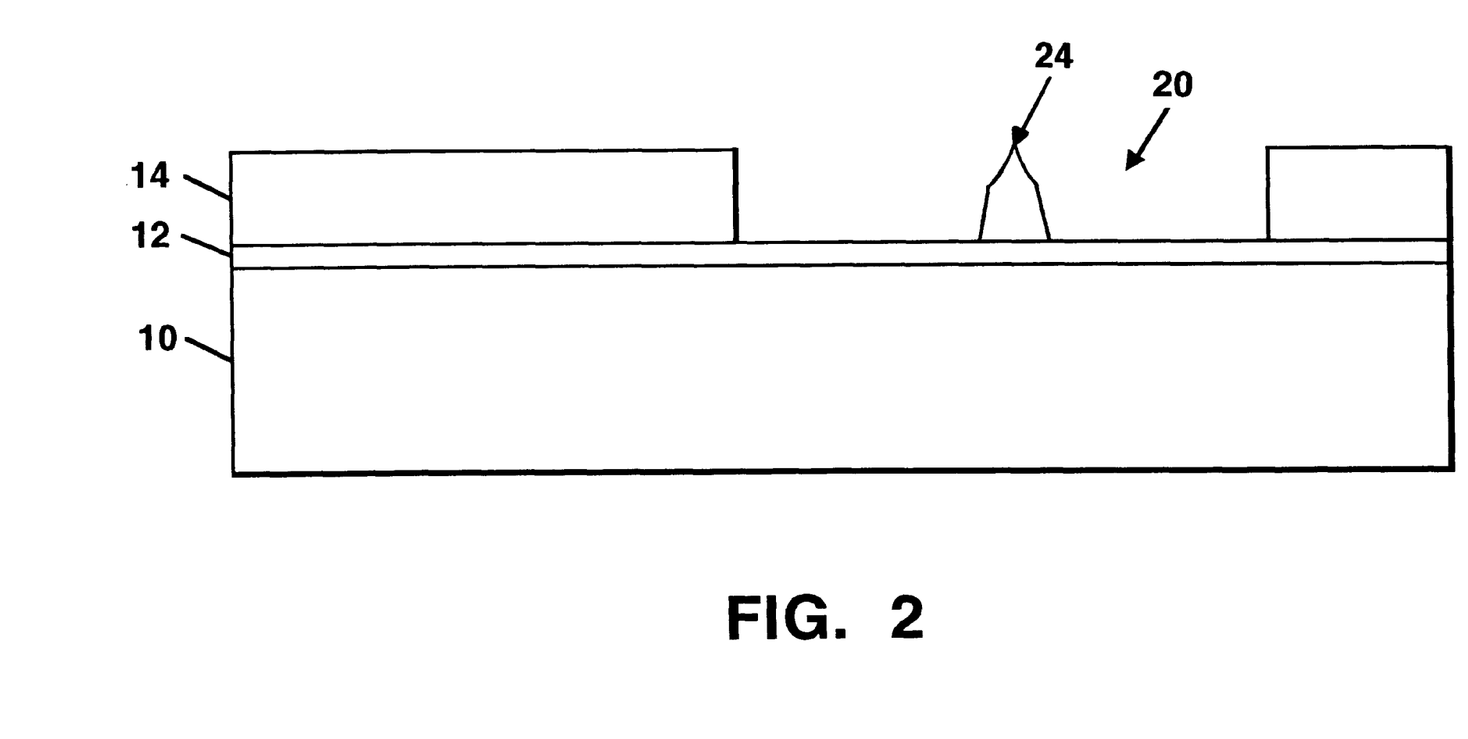
FIG. 2 is a cross sectional view of the device of FIG. 1 after tip sharpening.

Referring now to FIG. 2, the photoresist layer 18 and the oxide layer 16 have been removed, and the needle like elongated structure 20 has been sharpened to a fine point 24 by means of oxidation of the semiconductor layer 14, and stripping of the oxide, typically in HF acid solution. This is a process known as oxidative sharpening.

Figure 3:
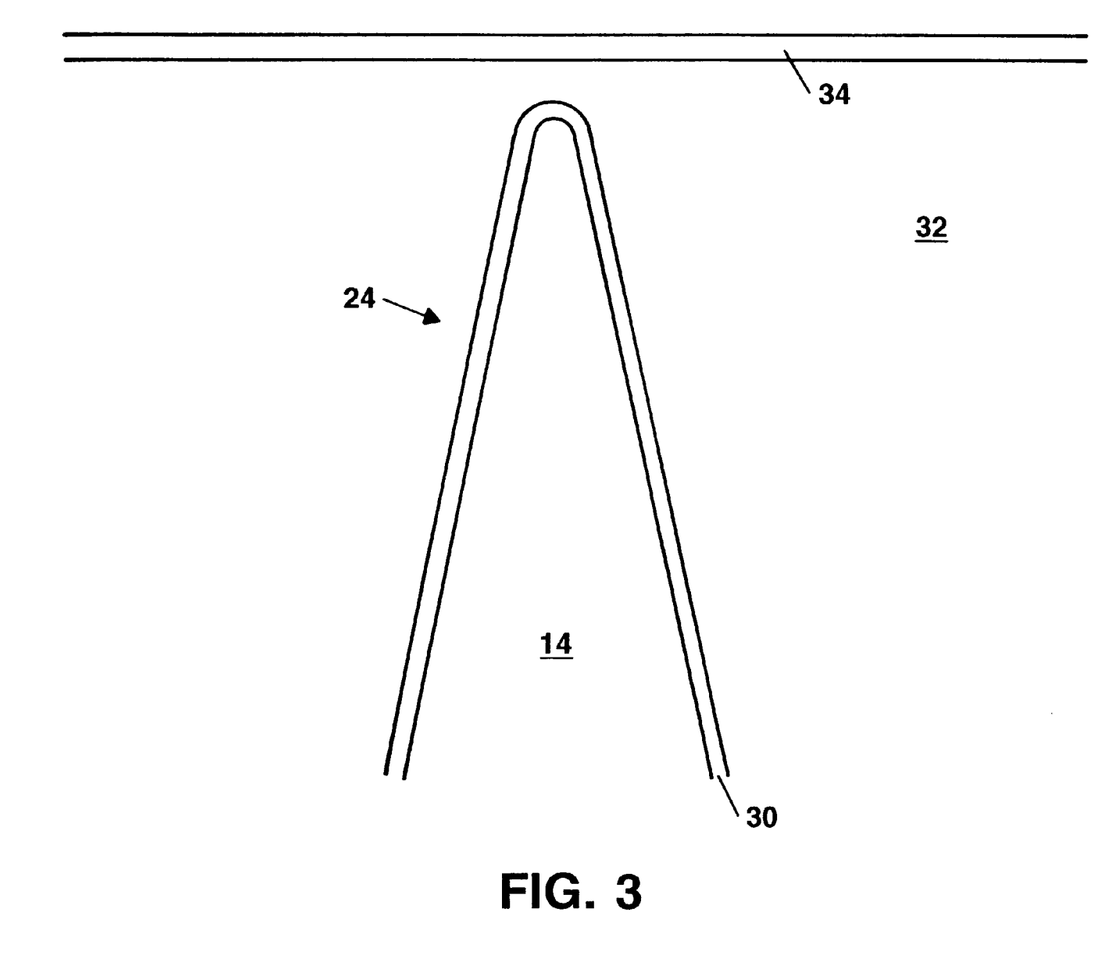
FIG. 3 is an enlarged cross-sectional view of the tip.

Referring now to FIG. 3, a close up cross section of the tip 24 of the needle 20 shows that the semiconductor layer 14 has been oxidized to form a layer 30. The layer 30 insulates the semiconductor 14, which in this preferred embodiment of the invention is heavily doped to act as one of the two metals required for the bimetallic thermocouple. A thick layer of a liquid organic material 32, preferably photoresist of a low viscosity, is deposited to a thickness that either completely or predominantly covers the tip 24. The low viscosity is chosen to provide poor step coverage to increase the probability that the tip 24 will be exposed. The parameters that affect the thickness of the organic material liquid 32 thickness include viscosity, polymer number, spin speed and spin speed ramp rate.

A partially solid film region 34 of the liquid 32 will form on the surface of liquid 32, either by continuing to spin the liquid 32 on the dispensing device, or by air or oven drying the liquid 32 to a semisolid state.

Figure 4:
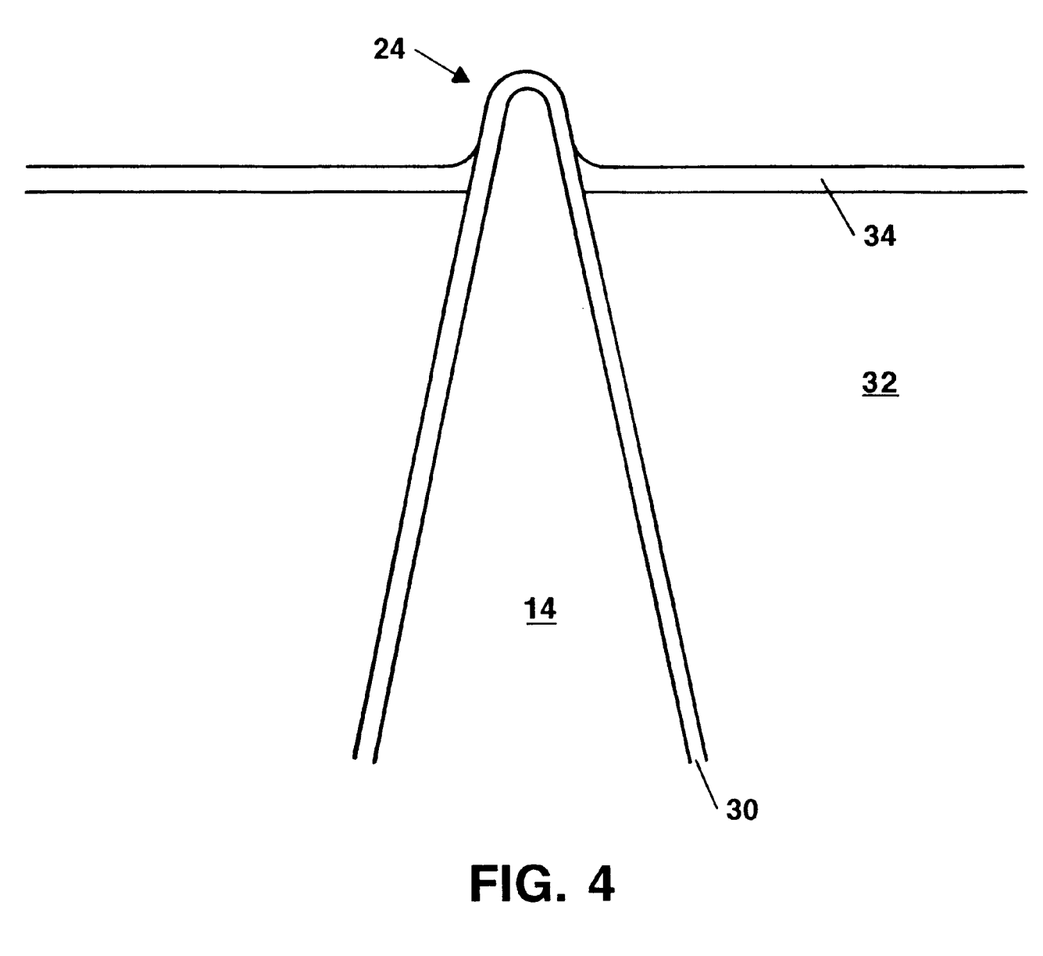
FIG. 4 is a cross-sectional view of the tip exposure.

Referring now to FIG. 4, the liquid 32 having the film 34, is again spun at a spin ramp rate and spin speed calculated to decrease the thickness of layer 32 to a point below the tip 24, thereby exposing the oxide 30 to etch. Alternative embodiments of the invention decrease the thickness of layer 32 by means of a controlled etch back, preferably an oxygen plasma, until either a preselected time has elapsed, or until a detector records the exposure of the tip 24. A preferred detector uses wide angle scattered laser light to detect the emergence of tip 24.

Figure 5:
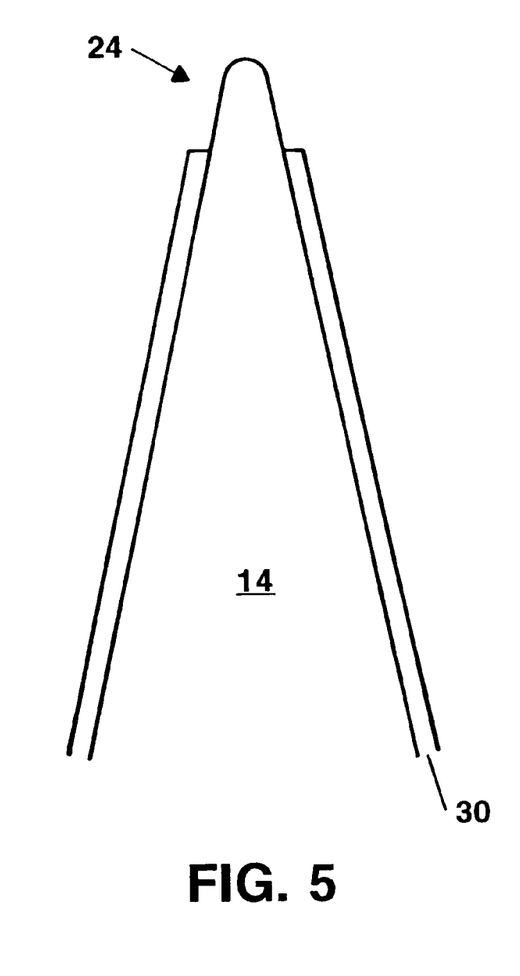
FIG. 5 is a cross-sectional view of the tip etching.

Referring now to FIG. 5, the oxide 30 has been etched from the tip 24 of the needle 20, and the liquid 32 has been stripped off, preferably by an oxygen plasma. The heavily doped semiconductor material 14 now has a controlled small area exposed to form the thermocouple for the microprobe.

Figure 6:
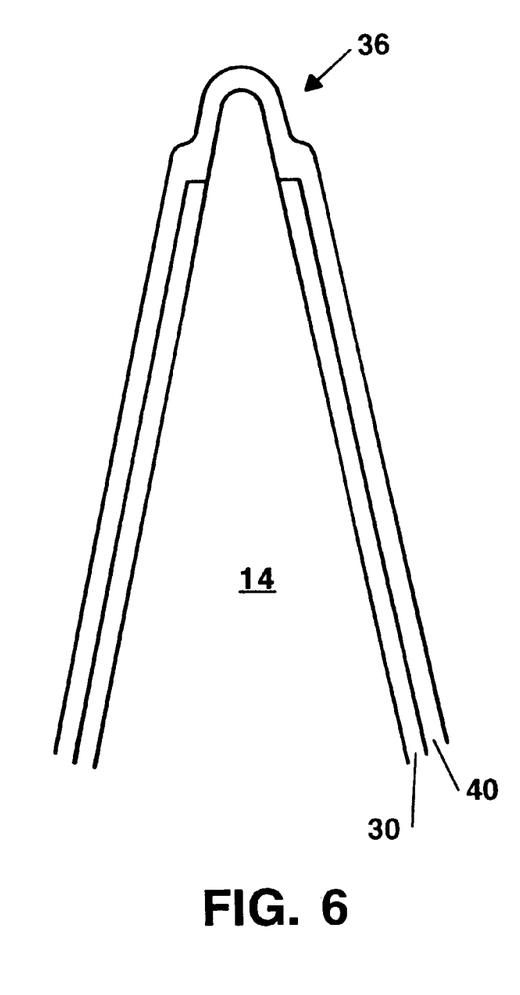
FIG. 6 is a cross-sectional view of the thermocouple tip in accordance with the invention.

Referring now to FIG. 6, the thermocouple 36 is formed by the junction of the semiconductor material 14 and a patterned metal layer 40, preferably made of gold.

Figure 7:
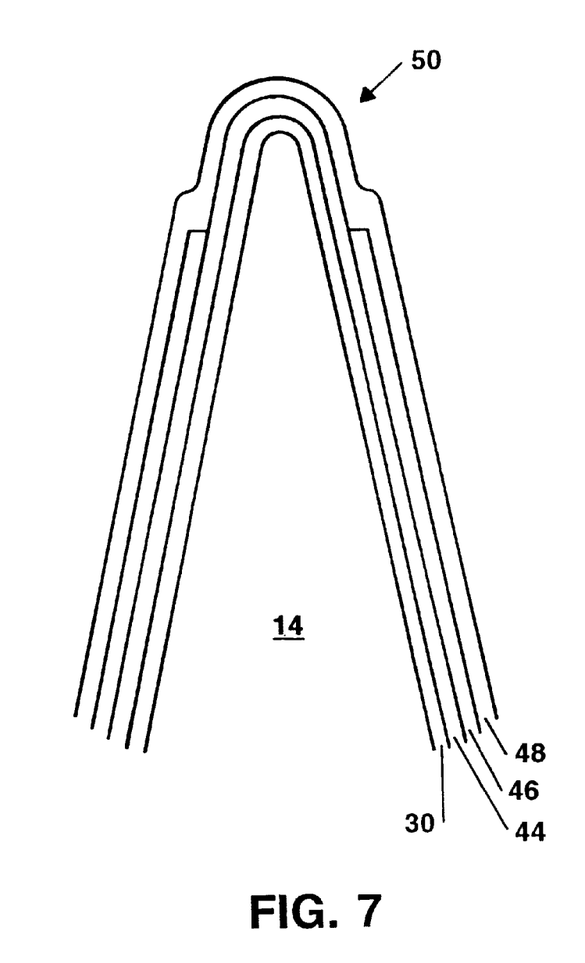
FIG. 7 is a cross-sectional view in accordance with an alternative embodiment of the invention.

Referring now to FIG. 7, an alternative embodiment of the thermocouple is shown wherein the semiconductor 14 does not act as one of the two metal layers and does not require a heavy doping level. Semiconductor layer 14 is covered with an insulating oxide layer 30, which is covered by a first metal layer 44, preferably a dual layer of titanium covered by palladium. The first metal layer is covered by an insulator layer 46, preferably a silicon dioxide layer, and exposed by the methods previously discussed to a second metal layer 48, preferably gold, thereby forming a bimetallic thermocouple 50, having a controlled small area.

Figure 8:
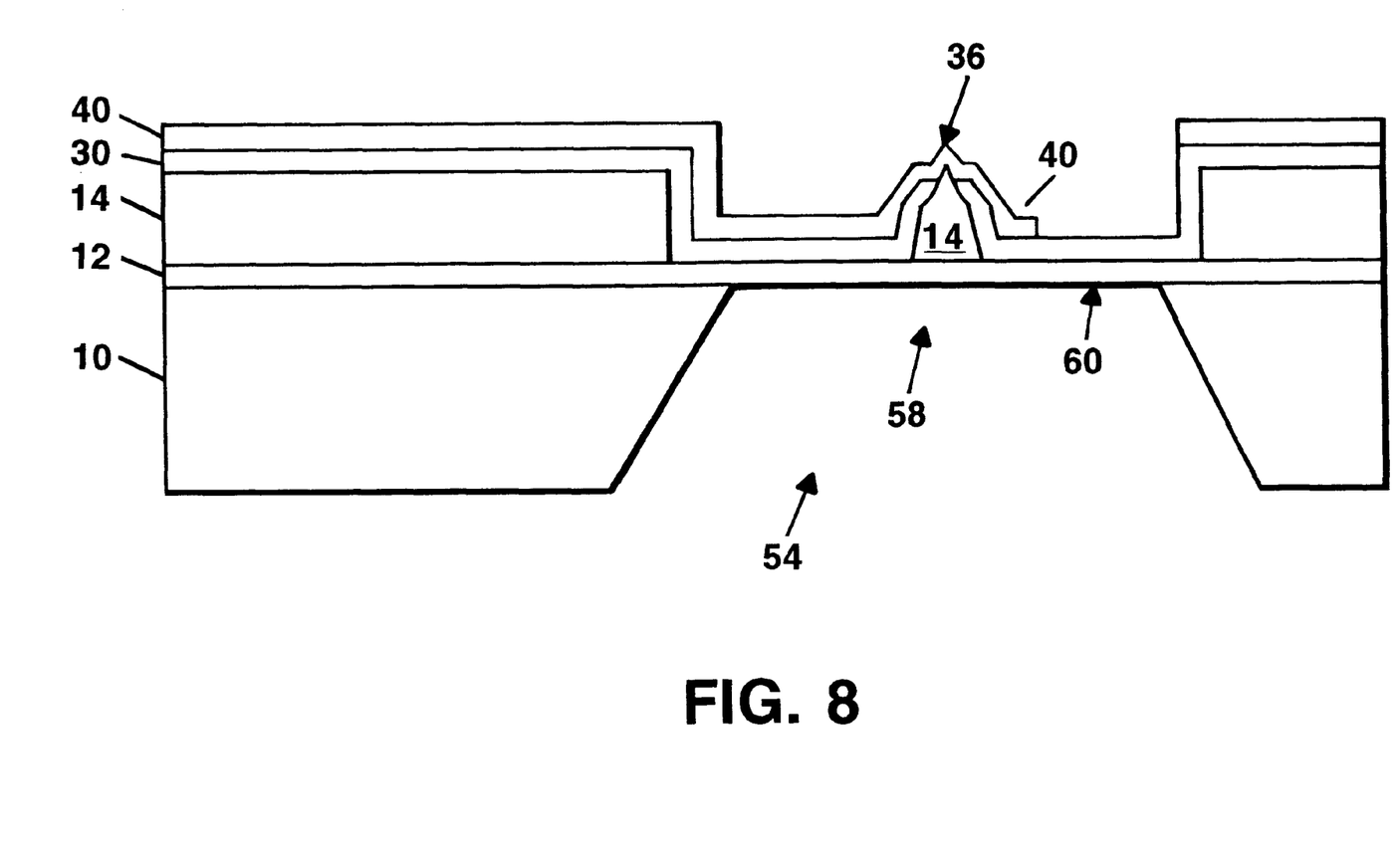
FIG. 8 is a cross-sectional view of the fabrication process in accordance with the invention.

Referring now to FIG. 8, the overall view of the fabrication process shown in FIG. 6, also shows the formation of a cantilevered structure 58 formed when the semiconductor material 10 is backside etched to form a void 54. An etch stopping layer such as heavily doped surface layer 12 may be used. The fabrication of the thermocouple 36 on cantilever 58 is completed by disconnecting the thermocouple 36 from the remaining semiconductor 10 at point 60, preferably by fracturing at the weak point 60. The thickness of surface layer 12 is preselected to have the structural properties desired, preferably about 3 microns for silicon.

Thus, in accordance with the invention, the formation of thermal microprobes with small contact areas on the tips of sharp needles results in improved scanning force microscope performance and in lower cost. In addition, the use of the present invention permits simpler fabrication procedures and large scale batch processing, resulting in lower costs. The resulting probe tips have large electrical and physical contacting areas for attachment to systems.

Having described a preferred embodiment of the invention, it will now be apparent to one of skill in the art that other embodiments incorporating its concept may be used. It is felt, therefore, that this invention should not be limited to the disclosed embodiment, but rather should be limited only by the spirit and scope of the appended claims.

What is claimed is:

1. A bimetallic thermocouple tip for a scanning force microscope comprising:
    a sharp semiconductor tip;
    a first dielectric layer disposed upon said semiconductor tip;
    a patterned first metal layer disposed upon said first dielectric layer;
    a second dielectric layer disposed upon said first metal layer;
    said second dielectric layer patterned to expose a predetermined sized region of said first metal layer through said second dielectric layer at an end of said semiconductor tip; and
    a second patterned metal layer disposed upon said second dielectric layer and contacting said first metal layer at said predetermined sized region through said second dielectric layer.

2. The thermocouple of claim 1 wherein said sharp semiconductor tip is sharpened by an oxidation process.

3. The thermocouple of claim 1 wherein said first metal layer is comprised of a titanium layer covered by a palladium layer; and
    said second metal layer is comprised of gold.

4. The thermocouple of claim 1 wherein said sharp semiconductor tip is one of a plurality of individual semiconductor tips, each individual one of said plurality disposed upon a separate one of a plurality of cantilevered structures; and
    said plurality of cantilevered structures disposed upon a semiconductor substrate.

5. The thermocouple of claim 4 wherein said second dielectric layer is patterned to expose a predetermined sized region of said first metal layer through said second dielectric layer, formed by the steps of:
    applying a liquid photoresist of a controlled viscosity to said semiconductor substrate;
    spinning said semiconductor substrate and said liquid photoresist for a first predetermined time and rotational speed, providing a layer of said liquid photoresist sufficient to cover said sharp semiconductor tip;

drying said liquid photoresist on said semiconductor substrate for a predetermined time, forming a semisolid film; and spinning said semiconductor substrate and said liquid photoresist for a second predetermined time and rotational speed such that said sharp semiconductor tip region protrudes through said photoresist film;

curing said photoresist film and said liquid photoresist by drying and polymerization;

removing said second dielectric layer from said first metal layer in that area of said sharp semiconductor tip that protrudes through said photoresist film; and removing said photoresist film from said semiconductor substrate.

* * * * *